(12) United States Patent
Antler

(10) Patent No.: US 7,424,952 B2
(45) Date of Patent: Sep. 16, 2008

(54) INTERDENTAL BRUSH PACKAGE

(75) Inventor: Steven M. Antler, Darien, CT (US)

(73) Assignee: Staino, LLC, Long Eddy, NY (US)

( * ) Notice: Subject to any disclaimer, the term of this patent is extended or adjusted under 35 U.S.C. 154(b) by 197 days.

(21) Appl. No.: 11/497,512

(22) Filed: Aug. 2, 2006

(65) Prior Publication Data

US 2008/0029409 A1 Feb. 7, 2008

(51) Int. Cl.
*B65D 83/08* (2006.01)
*B65D 65/00* (2006.01)
*A61B 19/02* (2006.01)
*A61C 15/00* (2006.01)

(52) U.S. Cl. .......... 206/362.4; 206/63.5; 206/369; 132/321; 229/87.01

(58) Field of Classification Search ........ 206/63.5, 206/362–362.3, 362.4, 369, 443, 581; 132/200, 132/321, 329; 229/87.01
See application file for complete search history.

(56) References Cited

U.S. PATENT DOCUMENTS

| | | | | |
|---|---|---|---|---|
| 1,615,200 | A * | 1/1927 | Shrum ............... | 229/87.01 |
| 2,313,629 | A * | 3/1943 | Dirienzo ............ | 206/112 |
| 2,839,184 | A * | 6/1958 | April ................ | 206/118 |
| 3,094,729 | A | 6/1963 | Dalton | |
| 3,438,486 | A * | 4/1969 | Pinkas ............... | 132/321 |
| 3,486,611 | A * | 12/1969 | Delphis .............. | 229/87.05 |
| 3,545,025 | A * | 12/1970 | O'Connell ......... | 206/362.1 |
| 3,951,460 | A | 4/1976 | Blankschein | |
| 5,090,080 | A | 2/1992 | Thuresson et al. | |
| 5,119,941 | A * | 6/1992 | Lepie ............... | 132/321 |
| D357,358 | S | 4/1995 | Schmotter et al. | |
| 5,414,890 | A | 5/1995 | Morando | |
| 6,158,444 | A * | 12/2000 | Weihrauch ......... | 132/321 |
| D505,790 | S | 6/2005 | Kline | |
| 7,033,101 | B2 | 4/2006 | Han | |
| 7,325,686 | B2 * | 2/2008 | Aldridge ........... | 206/460 |
| 2005/0255197 | A1 * | 11/2005 | Aldridge ........... | 426/108 |
| 2005/0255198 | A1 * | 11/2005 | Aldridge ........... | 426/108 |
| 2005/0266373 | A1 | 12/2005 | Lin | |
| 2006/0254609 | A1 * | 11/2006 | Kuo ................. | 132/321 |

FOREIGN PATENT DOCUMENTS

| | | | |
|---|---|---|---|
| JP | 2002191438 A * | 7/2002 | |
| JP | 2002-253343 | 9/2002 | |
| JP | 2003-250633 | 9/2003 | |

OTHER PUBLICATIONS

Translation of cited JP 2002-191438.*

* cited by examiner

*Primary Examiner*—Bryon P Gehman
(74) *Attorney, Agent, or Firm*—Shlesinger, Arkwright & Garvey LLP

(57) ABSTRACT

An interdental brush package comprises a plurality of interdental brushes, each having a handle and bristles connected to the handle; a container; the container including a pocket disposed at a bottom portion thereof; and the container including a backing extending from the pocket. The handles are disposed in the pocket and the bristles overlie the backing. A cover overlies the bristles and the backing, the cover having one end portion being receivable within the pocket.

13 Claims, 2 Drawing Sheets

INTERDENTAL BRUSH PACKAGE

FIELD OF THE INVENTION

The present invention is generally directed to interdental brushes, and particularly to an interdental brush package containing a plurality of interdental brushes packaged in a convenient container small enough to be carried in a person's pocket or purse.

OBJECTS AND SUMMARY OF THE INVENTION

It is an object of the present invention to provide an interdental brush package containing a number of interdental brushes disposed in a conveniently sized container that fits in a person's pocket or purse.

In summary, the present invention provides an interdental brush package, comprising a plurality of interdental brushes, each having a handle and bristles connected to the handle; a container; the container including a pocket disposed at a bottom portion thereof; and the container including a backing extending from the pocket. The handles are disposed in the pocket and the bristles overlie the backing. A cover overlies the bristles and the backing, the cover having one end portion being receivable within the pocket.

These and other objects of the present invention will become apparent from the following detailed description.

BRIEF DESCRIPTIONS OF THE DRAWINGS

DETAILED DESCRIPTION OF THE INVENTION

Figure 1:
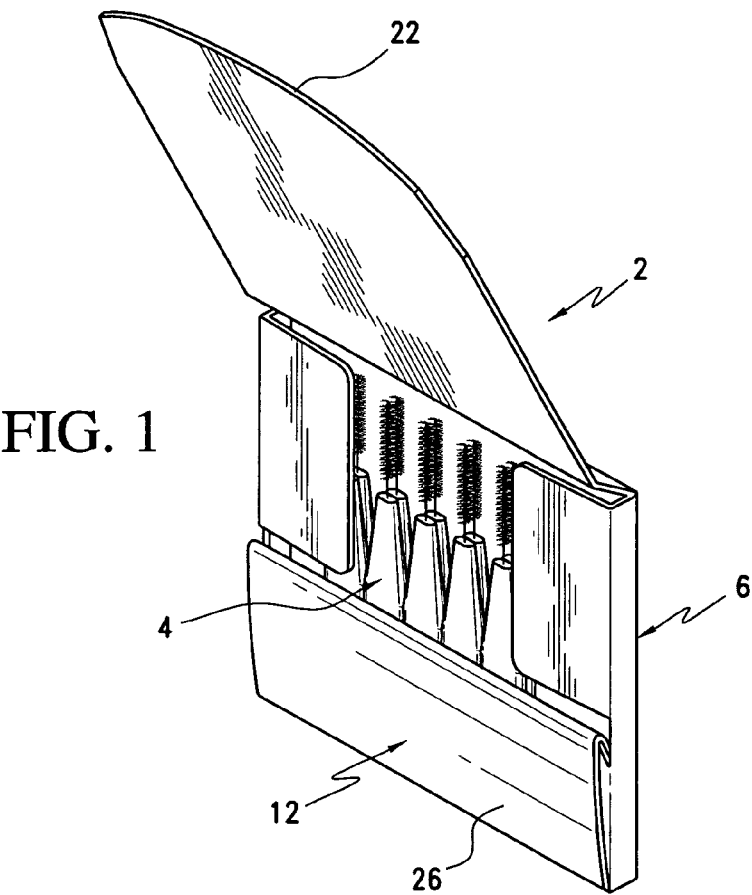
FIG. 1 is a perspective view of an interdental brush package made in accordance with the present invention.
Figure 2:
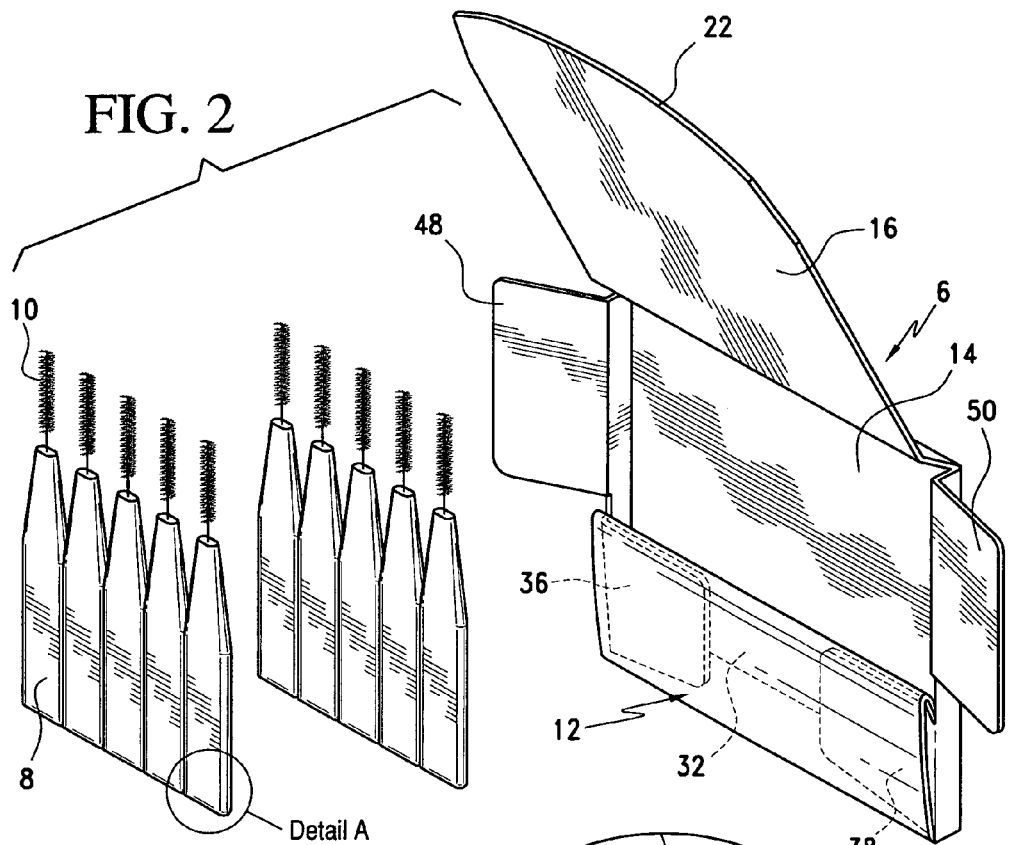
FIG. 2 is an assembly drawing showing the interdental brushes outside of the container.

An interdental brush package 2 made in accordance with the present invention is disclosed in FIGS. 1 and 2. The package 2 includes a plurality of interdental brushes 4 disposed within a container 6. Each of the interdental brushes 4 includes a handle 8 and bristles 10 connected to the handle. The handles 8 are disposed within a pocket 12 at a bottom portion of the container 6.

Referring to FIG. 2, the container 6 includes a backing 14 extending from the pocket 12. A cover 16 foldedly connected to the backing 14 along fold lines 18 and 20 overlies the brushes 4 (see FIG. 4). The fold lines 18 and 20 provide a hinge function for the cover 16. The cover 16 has a free end portion 22, which is receivable within the pocket 12. The end portion 22 is advantageously curved to facilitate insertion into the pocket 12.

Figure 5:
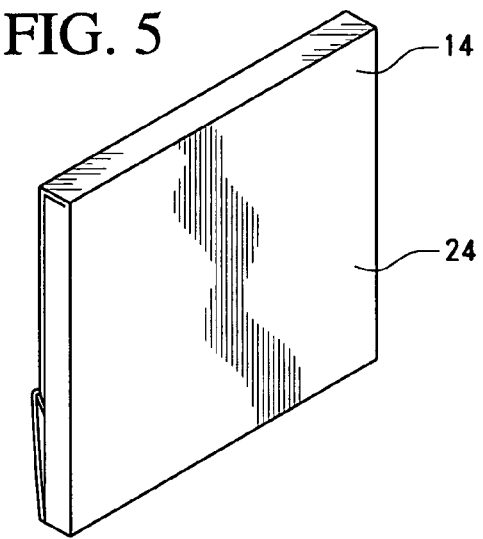
FIG. 5 is a rear perspective view of FIG. 4.
Figure 4:
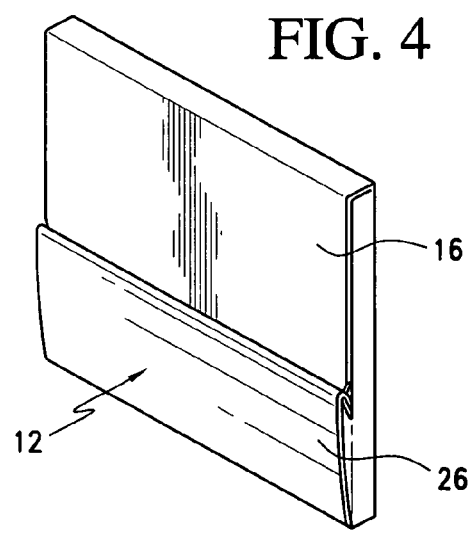
FIG. 4 is a front perspective view of the interdental brush package of FIG. 1 in a closed position.
Figure 3:
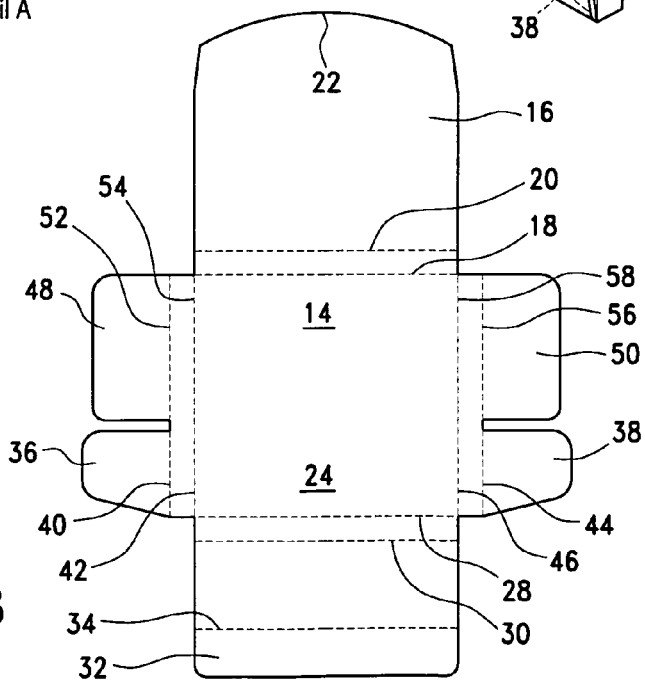
FIG. 3 is a layout of the container of FIG. 1.

Referring to FIGS. 3, 4 and 5, the pocket 12 includes a rear wall 24, which is integral with the backing 14, and a front wall 26 connected to the rear wall along fold lines 28 and 30. A flap 32 connected to the front wall 26 along fold line 34 is disposed within the pocket 12 and functions as a bias for urging the handles 8 and the cover end portion 22 towards the rear wall 24 and the backing 14, as shown in FIG. 4. The pocket 12 includes left and right flaps 36 and 38, respectively, connected to the rear wall 24 along fold lines 40 and 42, and 44 and 46.

The left and right flaps 36 and 38 are received within the pocket 12, underlying the flap 32 and the front wall 26. The left and right flaps 36 and 38 help hold up the front wall 26 and retain the flap 32 within the pocket 12.

Left and right flaps 48 and 50 are connected to the backing 14 along fold lines 52 and 54, and 56 and 58. The flaps 48 and 50 overlie the interdental brushes 4 and underlie the front cover 16. The flaps 48 and 50 help cover the interdental brushes 4 along the left and right edge portions of the container 6.

Figure 6:
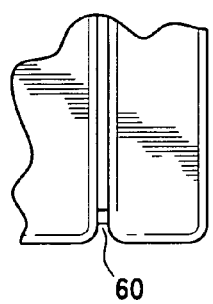
FIG. 6 is an enlarged portion of detail A taken from FIG. 2.

The handles 8 of the interdental brushes are advantageously flat to provide a comfortable grip for the user. The interdental brushes 4 are preferably removably connected to each other by means of a thin breakable plastic portion 60 between and connecting adjacent handles 8 (see FIG. 6), in a side-to-side or picket fence fashion. The flap 32 advantageously provides a smooth unbroken surface to the end portion 22 of the cover 16 as it is inserted into the pocket 12. The handles 8 may be made of plastic. The bristles 10 may be made as disclosed in U.S. Pat. No. 6,439,885, incorporated herein by reference.

The container 6 is preferably made from cardboard material, but other materials such as plastic may be used.

Although the interdental brushes 4 are shown in groups of two rows, one on top of the other, inside the container 6, they may also be packaged in a single row or in more than two groups of rows.

The interdental brush package 2 is conveniently sized to fit in a person's pocket or purse so that it may be carried conveniently and thus readily available for use, such as after eating a meal in a restaurant.

While this invention has been described as having preferred design, it is understood that it is capable of further modification, uses and/or adaptations following in general the principle of the invention and including such departures from the present disclosure as come within known or customary practice in the art to which the invention pertains, and as may be applied to the essential features set forth, and fall within the scope of the invention or the limits of the appended claims.

I claim:

1. An interdental brush package, comprising:
   a) a plurality of interdental brushes, each having a handle and bristles connected to said handle;
   b) a container;
   c) said container including a pocket disposed at a bottom portion thereof;
   d) said container including a backing extending from said pocket;
   e) said handles are disposed in said pocket;
   f) said bristles overlie said backing;
   g) a cover overlying said brushes and said backing, said cover having one end portion being receivable within said pocket;
   h) first and second flaps connected to respective left and right sides of said backing; and
   i) said flaps are operable about said respective left and right sides between a closed position overlying said bristles and an open position away from said bristles.

2. An interdental brush package as in claim 1, wherein said plurality of interdental brushes are disposed interconnected to each other by said handles in a side-to-side picket-fence fashion.

3. An interdental brush package as in claim 2, wherein said handles each include a breakable portion connected to an adjacent handle.

4. An interdental brush package as in claim 2, wherein said plurality of interdental brushes are disposed in two rows one on top of the other.

5. An interdental brush as in claim 1, wherein each said handle is flat.

6. An interdental brush package as in claim 1, wherein said cover is foldedly connected to said backing along fold lines.

7. An interdental brush package as in claim 1, wherein said container is made from cardboard.

8. An interdental brush package, comprising:
a) a plurality of interdental brushes, each having a handle and bristles connected to said handle;
b) a container;
c) said container including a pocket disposed at a bottom portion thereof;
d) said container including a backing extending from said pocket;
e) said handles are disposed in said pocket;
f) said bristles overlie said backing;
g) a cover overlying said brushes and said backing, said cover having one end portion being receivable within said pocket;
h) said pocket comprises a front wall and a rear wall;
i) said pocket includes a bias that tends to push said handles and said one end portion toward said rear wall;
j) said rear wall is integral with said backing;
k) said bias is a flap connected to said front wall and received within said pocket;
l) left and right flaps connected to left and right sides, respectively, of said backing and
m) said left and right flaps are disposed within said pocket and overlie said rear wall.

9. An interdental brush package, comprising:
a) a plurality of interdental brushes, each having a handle and bristles connected to said handle;
b) a container;
c) said container including a pocket disposed at a bottom portion thereof;
d) said container including a backing extending from said pocket;
e) said handles are disposed in said pocket;
f) said bristles overlie said backing;
g) a cover overlying said brushes and said backing, said cover having one end portion being receivable within said pocket;
h) said pocket comprises a front wall and a rear wall;
i) said pocket includes a bias that tends to push said handles and said one end portion toward said rear wall;
j) said rear wall is integral with said backing;
k) said bias is a flap connected to said front wall and received within said pocket;
l) left and right flaps connected to left and right sides, respectively, of said backing;
m) said left and right flaps are disposed within said pocket and overlie said rear wall; and
n) said bias underlies said left and right flaps.

10. An interdental brush package, comprising:
a) a plurality of interdental brushes, each having a handle and bristles connected to said handle;
b) a container;
c) said container including a pocket disposed at a bottom portion thereof;
d) said container including a backing extending from said pocket;
e) said handles are disposed in said pocket;
f) said bristles overlie said backing;
g) a cover overlying said brushes and said backing, said cover having one end portion being receivable within said pocket;
h) first and second flaps connected to and operable about respective left and right sides of said backing between an open position and a closed position; and
i) said flaps overlying said bristles in said closed position;
j) said cover overlying said left and right flaps in said closed position.

11. An interdental brush package, comprising:
a) a plurality of interdental brushes, each having a handle and bristles connected to said handle;
b) a container;
c) said container including a pocket for receiving said interdental brushes;
d) said container including a backing extending from said pocket;
e) a cover overlying said brushes and said backing, said cover having one end portion being receivable within said pocket;
f) said pocket including front and rear walls, said front wall including an upper edge;
g) left and right flaps connected to left and right sides, respectively, of said backing; and
h) said left and right flaps are disposed completely below said upper edge and within said pocket, said left and right flaps overlying said rear wall.

12. An interdental brush package, comprising:
a) a plurality of interdental brushes, each having a handle and bristles connected to said handle;
b) a container including a pocket for receiving said interdental brushes;
c) said container including a backing extending from said pocket;
d) a cover overlying said interdental brushes, said cover having one end portion being receivable within said pocket;
e) said pocket including a rear wall;
f) said pocket including a bias that tends to push said interdental brushes and said one end portion toward said rear wall;
g) left and right flaps connected to left and right sides, respectively, of said backing;
h) said left and right flaps are disposed within said pocket and overlie said rear wall; and
i) said bias underlying said left and right flaps.

13. An interdental brush package, comprising:
a) a plurality of interdental brushes, each having a handle and bristles connected to said handle;
b) a container including a pocket for receiving said interdental brushes;
c) said container including a backing extending from said pocket;
d) a cover overlying said interdental brushes and said backing, said cover having one end portion being receivable within said pocket;
e) first and second flaps connected to respective left and right sides of said backing; and
f) said flaps are operable about said respective left and right sides between a closed position overlying said interdental brushes and an open position away from said interdental brushes.

* * * * *